United States Patent
Prywes

(12) 
(10) Patent No.: US 9,132,032 B2
(45) Date of Patent: Sep. 15, 2015

(54) APPARATUS AND METHOD FOR PERFORMING OCULAR SURGERY

(76) Inventor: Arnold S. Prywes, Bethpage, NY (US)

( * ) Notice: Subject to any disclaimer, the term of this patent is extended or adjusted under 35 U.S.C. 154(b) by 0 days.

(21) Appl. No.: 13/271,090

(22) Filed: Oct. 11, 2011

(65) Prior Publication Data

US 2012/0130389 A1 May 24, 2012

Related U.S. Application Data

(60) Provisional application No. 61/391,330, filed on Oct. 8, 2010.

(51) Int. Cl.
| | |
|---|---|
| *A61F 9/00* | (2006.01) |
| *A61F 9/007* | (2006.01) |
| *A61B 17/02* | (2006.01) |
| *A61B 17/04* | (2006.01) |
| *A61B 17/06* | (2006.01) |

(52) U.S. Cl.
CPC ......... *A61F 9/00736* (2013.01); *A61B 17/0231* (2013.01); *A61B 17/06066* (2013.01); *A61B 17/0487* (2013.01); *A61B 17/06* (2013.01); *A61B 17/06061* (2013.01); *A61B 2017/0472* (2013.01); *A61B 2017/06071* (2013.01)

(58) Field of Classification Search
CPC .................... A61B 17/0231; A61B 17/06066; A61F 9/00736
USPC .................................. 623/4.1–6.12; 606/107
See application file for complete search history.

(56) References Cited

U.S. PATENT DOCUMENTS

| | | | | |
|---|---|---|---|---|
| 2,591,063 | A * | 4/1952 | Goldberg | 606/231 |
| 2,653,327 | A * | 9/1953 | Allen et al. | 623/4.1 |
| 3,608,095 | A * | 9/1971 | Barry | 128/898 |
| 4,037,589 | A * | 7/1977 | McReynolds | 600/209 |
| 4,321,916 | A * | 3/1982 | McKee | 600/209 |
| 4,479,802 | A * | 10/1984 | Anis | 604/275 |
| 4,573,998 | A * | 3/1986 | Mazzocco | 128/898 |
| 4,643,178 | A * | 2/1987 | Nastari et al. | 606/74 |
| 4,813,957 | A * | 3/1989 | McDonald | 606/107 |
| 5,002,563 | A * | 3/1991 | Pyka et al. | 606/222 |
| 5,318,011 | A * | 6/1994 | Federman et al. | 600/236 |
| 5,441,040 | A * | 8/1995 | Williams, Jr. | 600/236 |
| 5,474,557 | A * | 12/1995 | Mai | 606/78 |
| 5,972,024 | A * | 10/1999 | Northrup et al. | 606/232 |
| 6,299,618 | B1 * | 10/2001 | Sugiura | 606/107 |
| 6,352,542 | B1 * | 3/2002 | Snyder | 606/148 |
| 6,500,181 | B1 * | 12/2002 | Portney | 606/107 |

(Continued)

FOREIGN PATENT DOCUMENTS

WO    WO 2012/048348 A1 *  4/2012 ............ A61B 19/00

*Primary Examiner* — Paul Prebilic
(74) *Attorney, Agent, or Firm* — Ladas & Parry LLP

(57) ABSTRACT

A method and apparatus for performing eye surgery. A deformable body having shape memory retentive properties is formed with one or more open loops. The body is longitudinally stretched so that it can follow a needle through a small caliber needle track formed in the cornea, into the anterior chamber in front of the iris. There, the body has relaxed and reverted to its original shape. The needle is of such size that the needle track self-closes and no closure stitch is needed. Two sutures are connected to opposite ends of the body and one of the sutures connects the body to the needle. After the body is in the pupil of the iris, the loop openings face the wall of the iris and then the sutures are pulled to displace the body and press it against the wall of the iris to dilate the pupil.

21 Claims, 20 Drawing Sheets

(56) References Cited

U.S. PATENT DOCUMENTS

| | | | |
|---|---|---|---|
| 6,561,974 B1* | 5/2003 | Grieshaber et al. | 600/206 |
| 6,913,607 B2* | 7/2005 | Ainsworth et al. | 606/151 |
| 8,500,760 B2* | 8/2013 | McLawhorn | 606/151 |
| 2001/0018593 A1* | 8/2001 | Nguyen et al. | 606/151 |
| 2002/0091306 A1* | 7/2002 | Juan et al. | 600/235 |
| 2004/0111099 A1* | 6/2004 | Nguyen et al. | 606/139 |
| 2007/0027541 A1* | 2/2007 | Aharoni et al. | 623/6.41 |
| 2008/0243139 A1* | 10/2008 | Dusek | 606/107 |
| 2012/0130389 A1* | 5/2012 | Prywes | 606/107 |
| 2012/0232351 A1* | 9/2012 | Assia et al. | 600/217 |
| 2014/0039270 A1* | 2/2014 | Merriam et al. | 600/217 |

\* cited by examiner

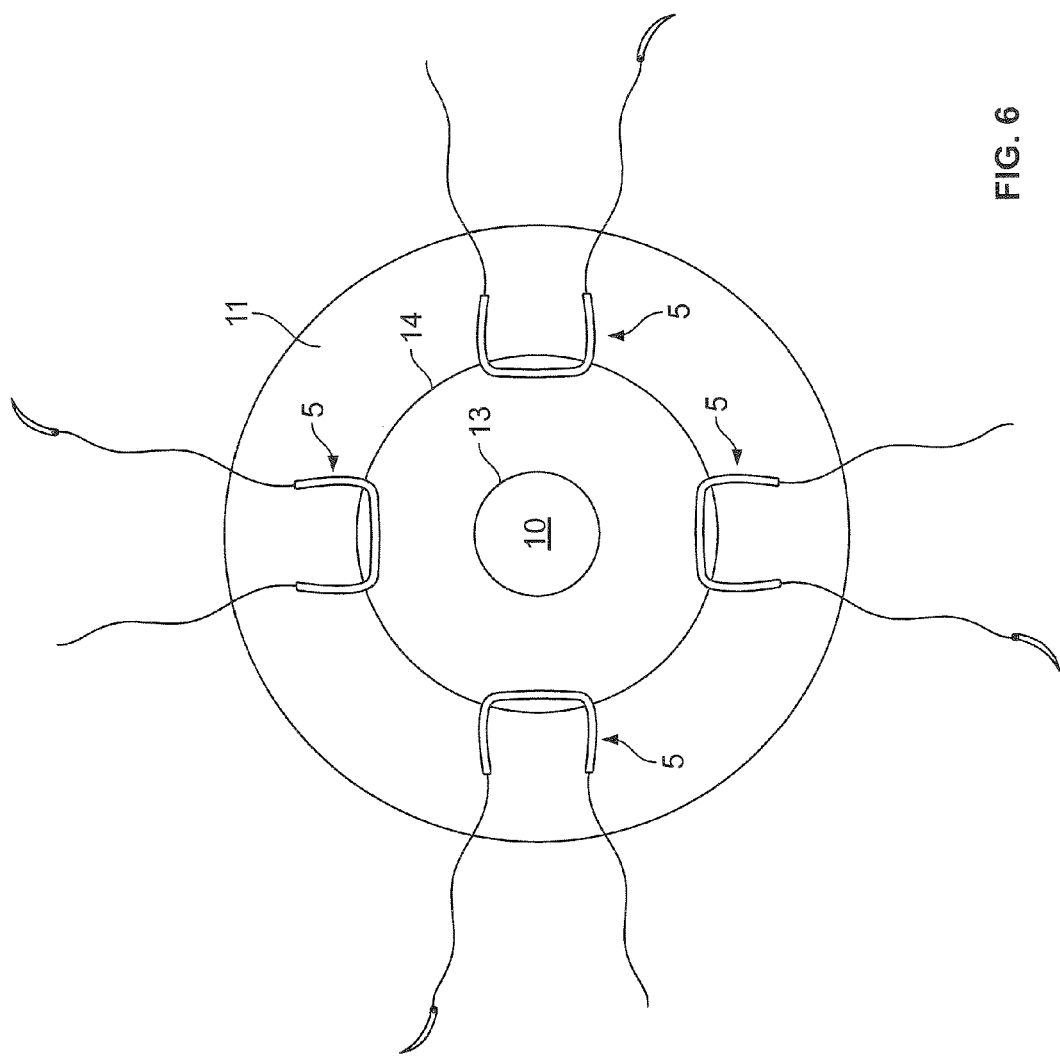

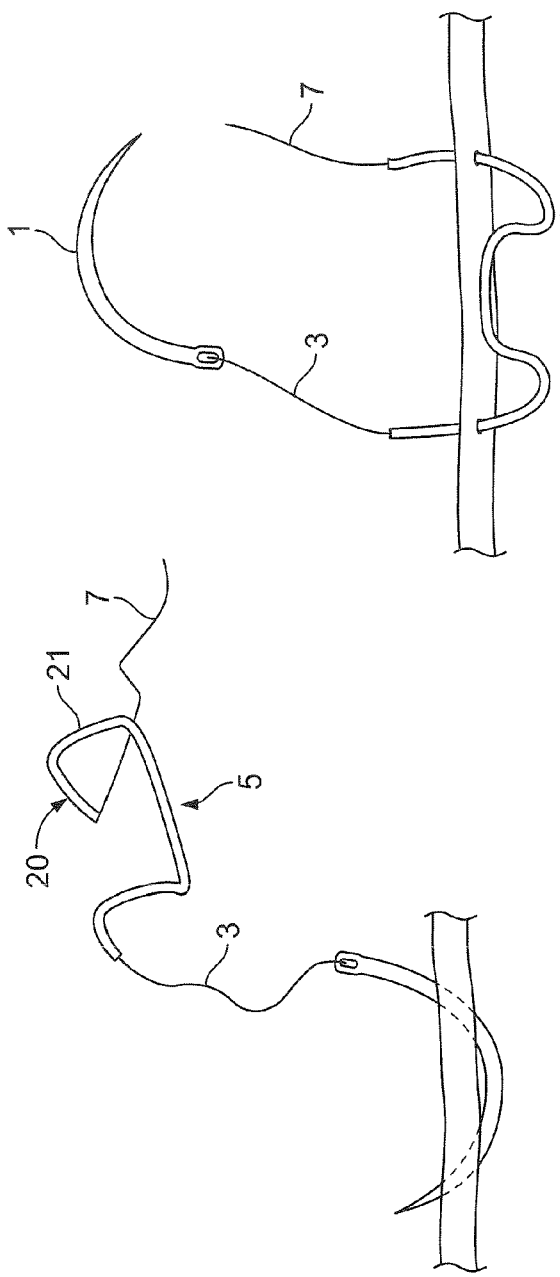
FIG. 7A
FIG. 7B
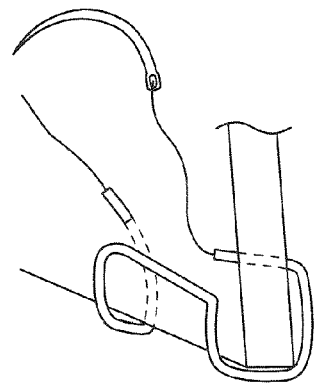
FIG. 7E
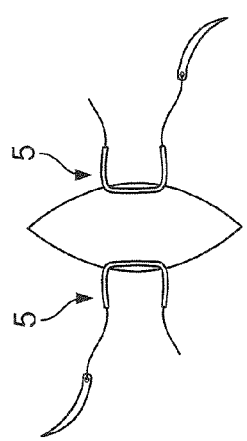
FIG. 7D
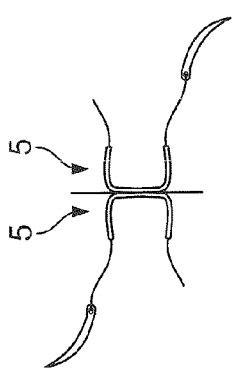
FIG. 7C

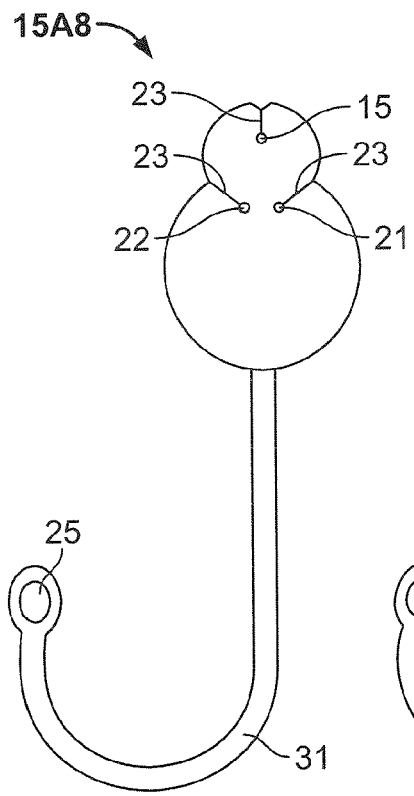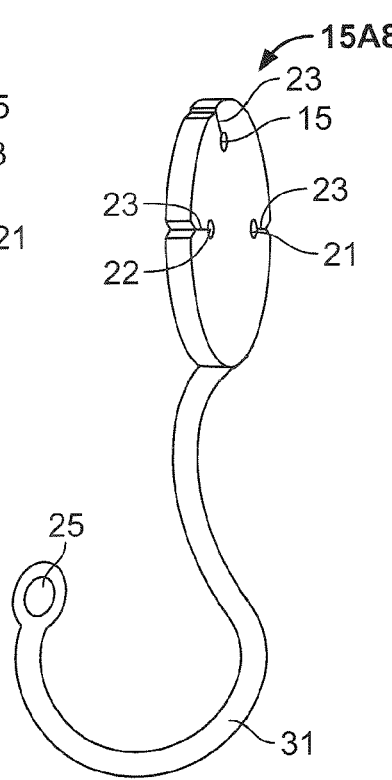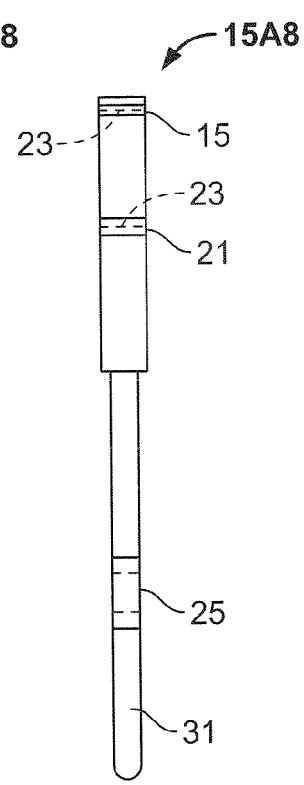
FIG. 15A  FIG. 15B  FIG. 15C
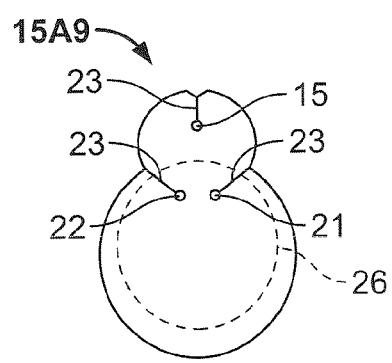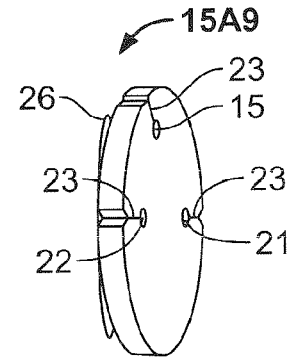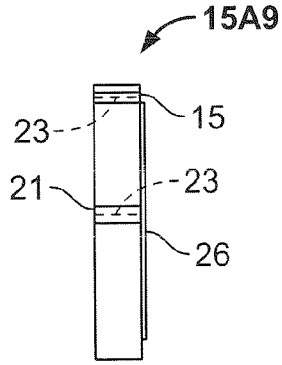
FIG. 16A  FIG. 16B  FIG. 16C

APPARATUS AND METHOD FOR PERFORMING OCULAR SURGERY

FIELD OF THE INVENTION

The invention relates to methods and apparatus for genera; surgery, especially ocular surgery and in particular for cataract surgery.

The invention further relates to a device used in such surgery for pupil dilation, for lens capsule dilation and/or for connecting or stabilizing an intraocular lens.

The invention also relates to apparatus for cinch locking the device during surgery or as a tether to secure the device when it remains in the eye.

BACKGROUND AND PRIOR ART

Methods for retracting tissues to improve visualization or prevent trauma to tissues impinging on a surgical site have been used for centuries. Optical instruments, such as speculums or retraction devices require a surgical opening to be made for their insertion thereby adding to the number of wounds required to accomplish proper exposure.

Heretofore these devices have been placed through small or large incisions in order to bring retracting or hooking surface to bear against the tissue to be retracted.

For cataract surgery a large pupil of 6 mm or more is required. When pupils do not dilate well due to the presence of adhesions, inability of the iris musculature to respond to pharmacologic mydriasis, or for other reasons, a mechanical method of enlarging the pupil is necessary. Stretching the iris has been the most common methodology in the last thirty years.

Speculums were employed in the past for retracting the iris during intracapsular cataract surgery whereby removal of the entire lens utilizing an incision of 8-10 mm or larger was required. The Rosenbaum Drews iris retractor was one such example. The surgeon must hold the retractor with one hand while an assistant lifted the cornea and the surgeon removed the lens with a cryoprobe or other such lens removal device with the dominant hand. Models for left and right handed surgeons were designed. With the onset of modern small incision surgery 1.5-6 mm incisions have been employed. The size limitations of a small incision and the presence of a small pupil required that the iris be cut and moved out of the way, stretched using (Kuglen) hooks, (Beehler) pupil stretchers or that a small (peripheral) or large section of the iris be removed (sector iridectomy) to facilitate cataract removal. Recently the presence of a condition whereby the iris prolapses through the small incision has been described. This condition has been given the name "intraocular floppy iris syndrome" or IFIS. Enlarging the incision or introducing instruments into the eye requires that the pupil remain dilated and the iris be kept away from the incision. Intraocular hooks for retracting the iris or lens capsule developed by Makool are introduced through individual small incisions. Four or five of these incisions and hooks are required to adequately retract the iris. With multiple incisions and multiple hooks to retract the iris, insertion and removal may be problematic. The hooks may rotate into the iris stroma damaging the iris and causing bleeding thereby making surgery more difficult. Insertion and removal of the hooks is technically difficult and many surgeons avoid them for this reason. The introduction of pupillary rings developed by Milverton "Perfect Pupil™", Malyugin "Malyugin ring" is another method for retracting the iris through the incision which is made for cataract removal. An expanding ring is inserted through the small cataract incision. The expense of the device, and the necessity for learning a new methodology with specially developed insertion and removal tools has limited their use.

SUMMARY OF THE INVENTION

An object of the invention is to provide a speculum or retractor and associated methods for its utilization which avoids the need for hooks or other bulky instruments and their associated incisions as explained above in respect of the prior art.

A particular object of the invention is to provide a speculum or retractor which can be introduced into the eye without need for an incision or any closure stitch.

The terms speculum, retractor and speculum retractor are used interchangeably and refer to the same element.

A further object of the invention is to provide such a speculum or retractor which is made of a deformable material that has shape retentive memory so that it can be installed in a collapsed, deformed state through a needle track into a position adjacent to the iris where it expands to its original state to accomplish various purposes in the eye surgery.

In accordance with the invention, the speculum is secured to a suture connected to a needle. The needle is inserted through the cornea into the anterior chamber of the eye and exits from a corneal site several millimeters from the entry site. This results in the speculum remaining in the anterior chamber with suture ends external to the eye. The needle diameter is larger than the deformed speculum allowing easy passage of the flexible speculum through the needle track. The speculum can then be manipulated in the anterior chamber through an original cataract incision or a small paracentesis to engage the iris. The suture is pulled up to a desired position of the speculum resulting in dilation of the iris and the pupil being secured. Several of the sutures with speculums are placed to produce the desired degree of dilation of the iris.

The speculum retractors may also be used to engage the capsular bag, if required, for zonular weakness or absence, or to stabilize a subluxed posterior chamber intraocular lens. The speculum retractors may also be used to support a customized intraocular lens in the absence of capsular or iris support.

The speculum of the invention has use in general laparoscopic and other forms of surgery of various sizes in which retraction is important for visualization of surgical wounds.

DESCRIPTION OF THE FIGURES OF THE DRAWING

FIGS. 3A-3D diagrammatically illustrate progressively the deformation of the retractor for its entry and passage through the needle track.

FIG. 6 diagrammatically illustrates a pupil dilated by four retractors.

FIGS. 7A-7E diagrammatically illustrate the retractors for tissue retraction.

FIGS. 15A-15C further illustrate suture cinch lock discs.

FIGS. 16A-16C diagrammatically illustrate cinch lock discs.

DETAILED DESCRIPTION

Figure 1:
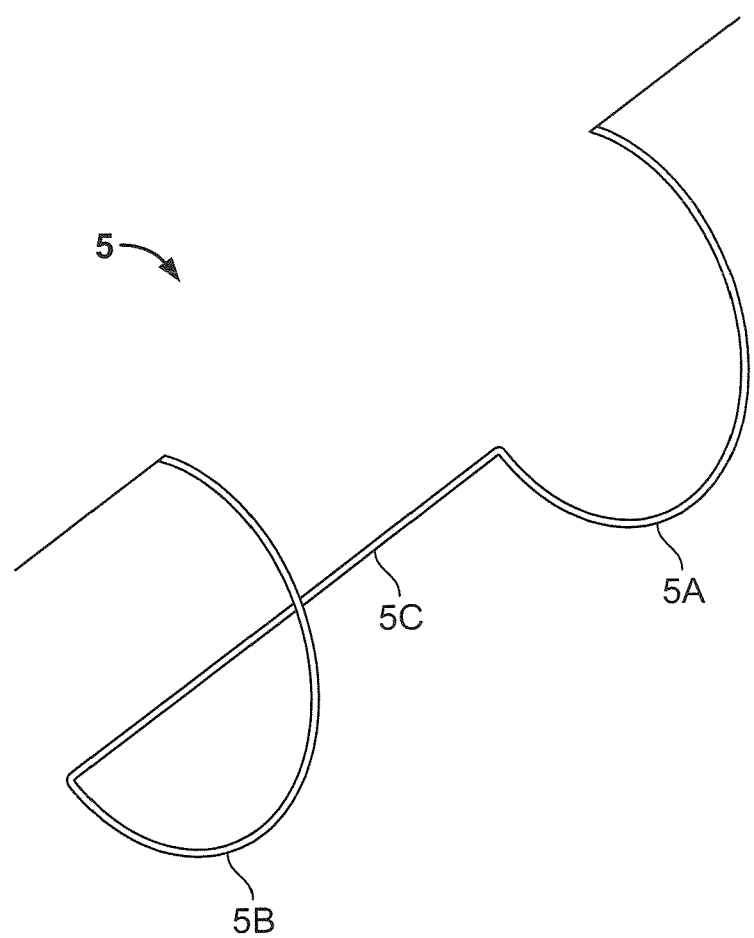
FIG. 1 is a perspective view of one embodiment of a speculum or retractor according to the invention.

Referring to the drawing and particularly to FIGS. 1-6, therein there is seen a portion of an eye of a patient adapted to undergo cataract surgery. In the course of the surgery, an optical instrument in the form of a treatment device will be used and described in greater detail subsequently and which will include and be referred to hereafter, in equivalent terms, as a speculum, retractor or speculum retractor.

The speculum or retractor is made as a deformable body of shape retentive memory material that is capable of being deformed to a stretched, collapsed position and able to return to its original shape when relaxed and no longer deformed. The body can be a natural biometric material, such as titanium, stainless steel or the like or synthetic materials, such as polypropylene or Nylon provided that it is inert to the human body.

FIG. 1 diagrammatically illustrates a treatment device comprising a needle 1 of curved shape with a pointed end 2 for piercing body tissue. Connected to the needle, for example, by swaging, or a link coupling, is a flexible suture 3 of conventional suturing material, such as polypropylene or titanium thread. The thread is connected at 4 to one end of the speculum or retractor 5 by swaging or a link connection or the like. At the opposite end 6 of the retractor 5, it is connected to a further length of suture 7.

In order for the speculum to be brought to an operative position in the eye, the needle pierces the cornea 8 (only a portion of which is shown) of the eye and transports the suture 3 and the speculum 5 therewith into the anterior chamber 9 of the eye adjacent to the pupillary aperture or pupil 10 in the iris 11 of the eye.

In the course of the travel of the needle 1 through the cornea 8, the needle forms a needle track 12 in the cornea, through which the suture 3 and the deformed, collapsed speculum (to be described in more detail subsequently) pass. The needle 1 is of sufficiently small diameter that the needle track 12 self-closes and a closure stitch is unnecessary.

FIG. 1 shows the retractor 5 in its initial undeformed state. As shown, the retractor is formed as a continuous length of wire material to constitute a wire-form body and includes two loop members 5A, 5B connected by a connecting portion 5C. The loop members 5A and 5B are partial loops that are adapted for engaging the iris or for engaging a lens, or lens capsule as will be explained later. One lower end of loop member 5A, representing one end 4 of retractor 5, is connected to suture 3. An opposite end 6 of retractor 5 is connected to the suture 7. The loop members are formed as predominantly open semi-circular shape. The loops can have other shapes other than semi-circular as long as it has an opening for insertion of the iris and a curved bearing surface for contacting the iris and applying lifting pressure thereagainst. For example, the loop member can be oval or rectangular with a rounded top or any combination thereof.

Figure 2:
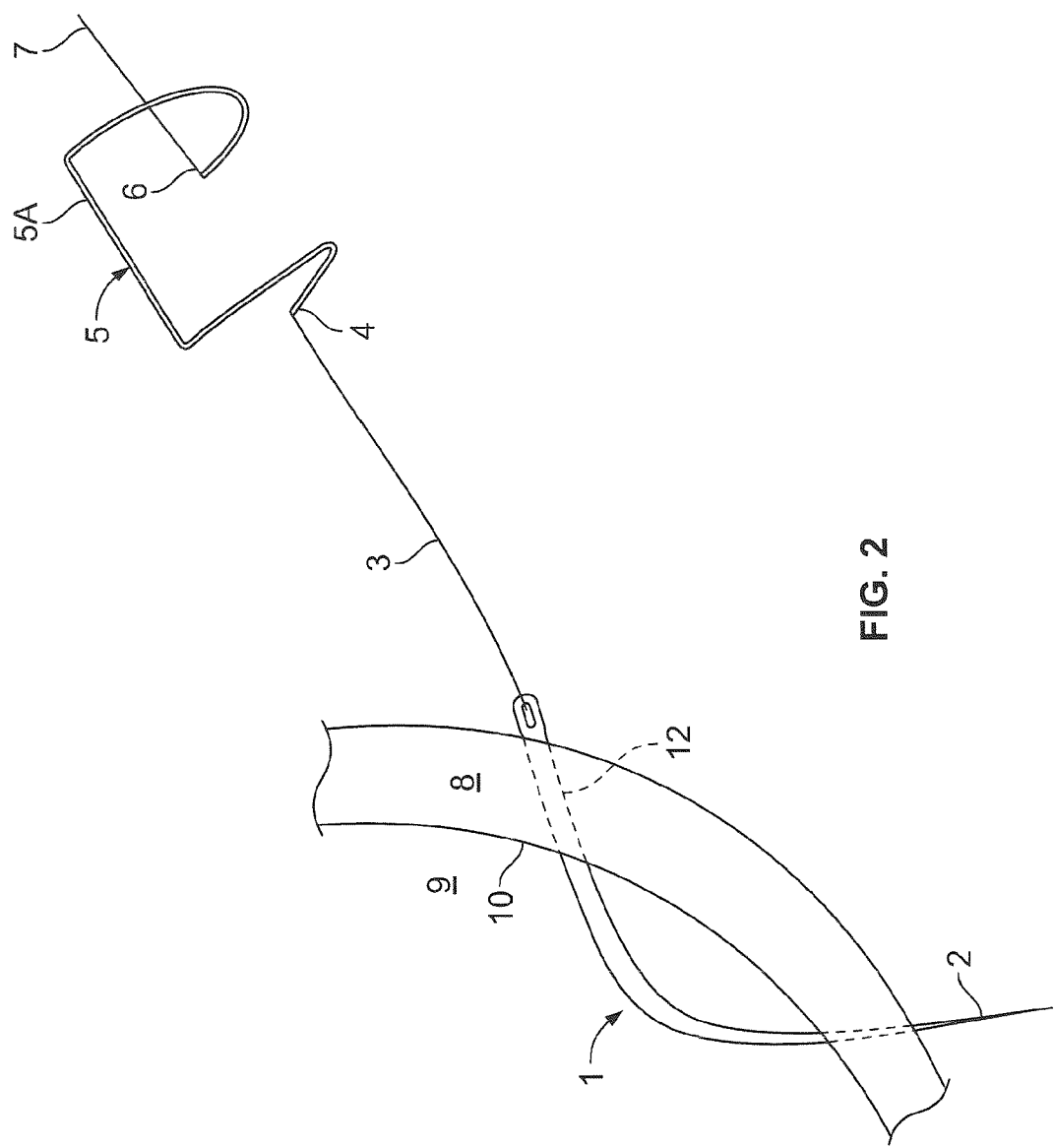
FIG. 2 shows another embodiment of the speculum or retractor according to the invention.
Figure 3:
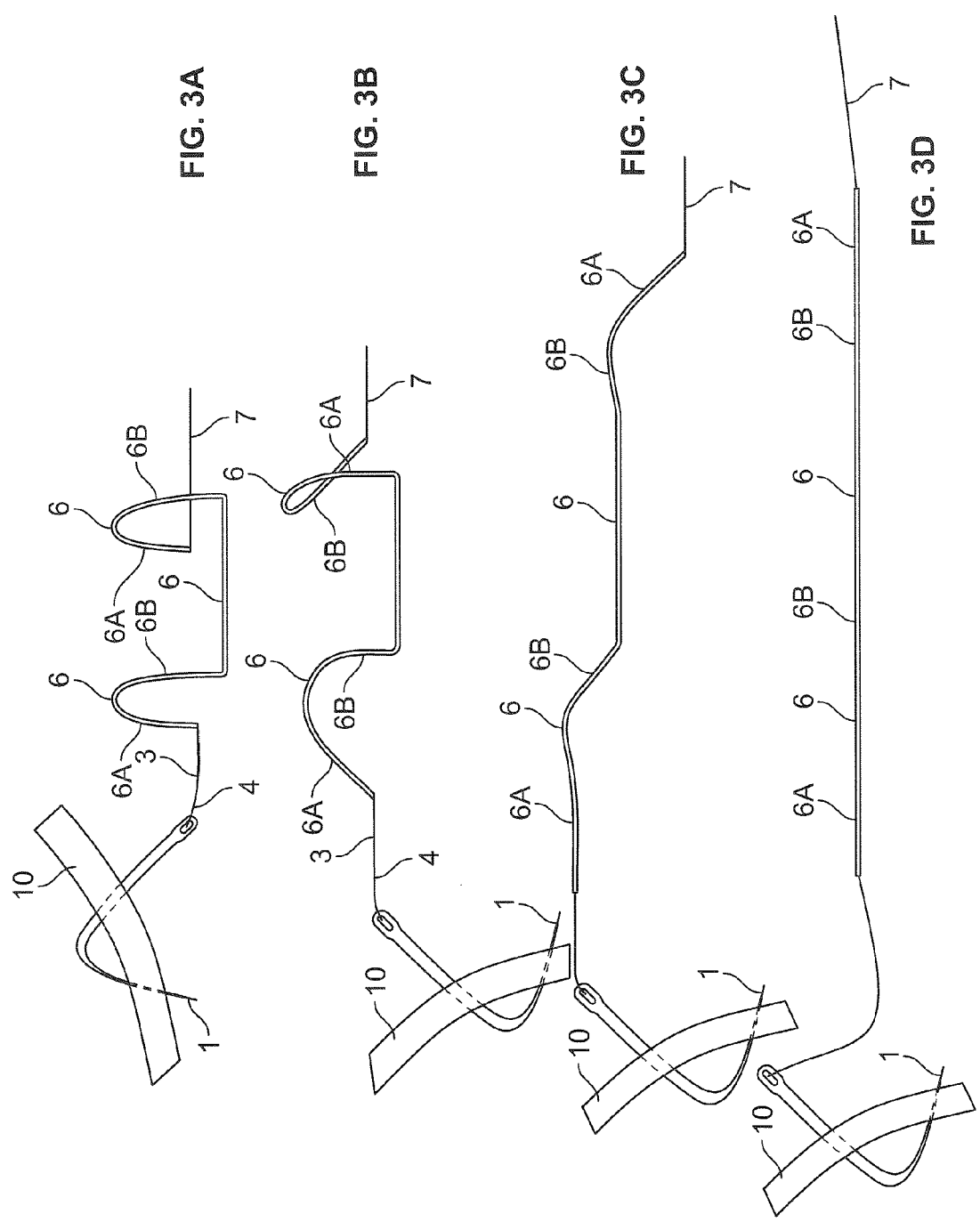
FIG. 3 diagrammatically illustrates the retractor of FIG. 1 assembled with a needle and a suture for passing through the cornea.

FIG. 2 shows another embodiment of the retractor in which only a single loop member 5A is provided. As in the previous embodiment, the retractor 5 is connected at its ends to both sutures 3 and 7. The connection of the suture 3 to the lower end of the loop member is made through a reverse bend at the lower end of the loop member.

The retractor is deformed as shown in FIGS. 3A-3C by applying tension thereto by pulling on the needle 1 in one direction and by pulling on the suture 7 in the opposite direction to stretch and deform the retractor. The needle is pulled through the cornea 9 by a conventional needle holder (not shown) to form the needle track 12. The suture 3, the deformed retractor and suture 7 follow in succession. The sequence of the deformation of retractor 5 is shown in FIGS. 3A-3C. It is seen in particular in FIG. 3C that the retractor is substantially in flattened state when fully deformed to enable its passage through the needle track 12. When the retractor has been introduced into the anterior chamber 9 and the needle has exited from the cornea at an exit site several millimeters from the needle entry site, the needle 1 can be separated from the suture 3 so that both ends of the sutures extend outside the cornea.

Dimensions

A normal corneal diameter is between 11 and 13.5 mm, normal pupil diameter is between 2 and 4 mm and the needle length is between 9 and 15 mm. The retractor in its normal undeformed state has a length of 2-3 mm, a height of 0.5-1 mm and a width of 0.5-1 mm. In its deformed flattened state the retractor has a length of 7-8 mm. The retractor has a wire diameter of 0.1-0.2 mm although it need not be circular but can be slightly oval or flattened. The retractor has sufficient strength and rigidity to apply force to the iris to dilate the pupil as will be shown later.

Figure 4:
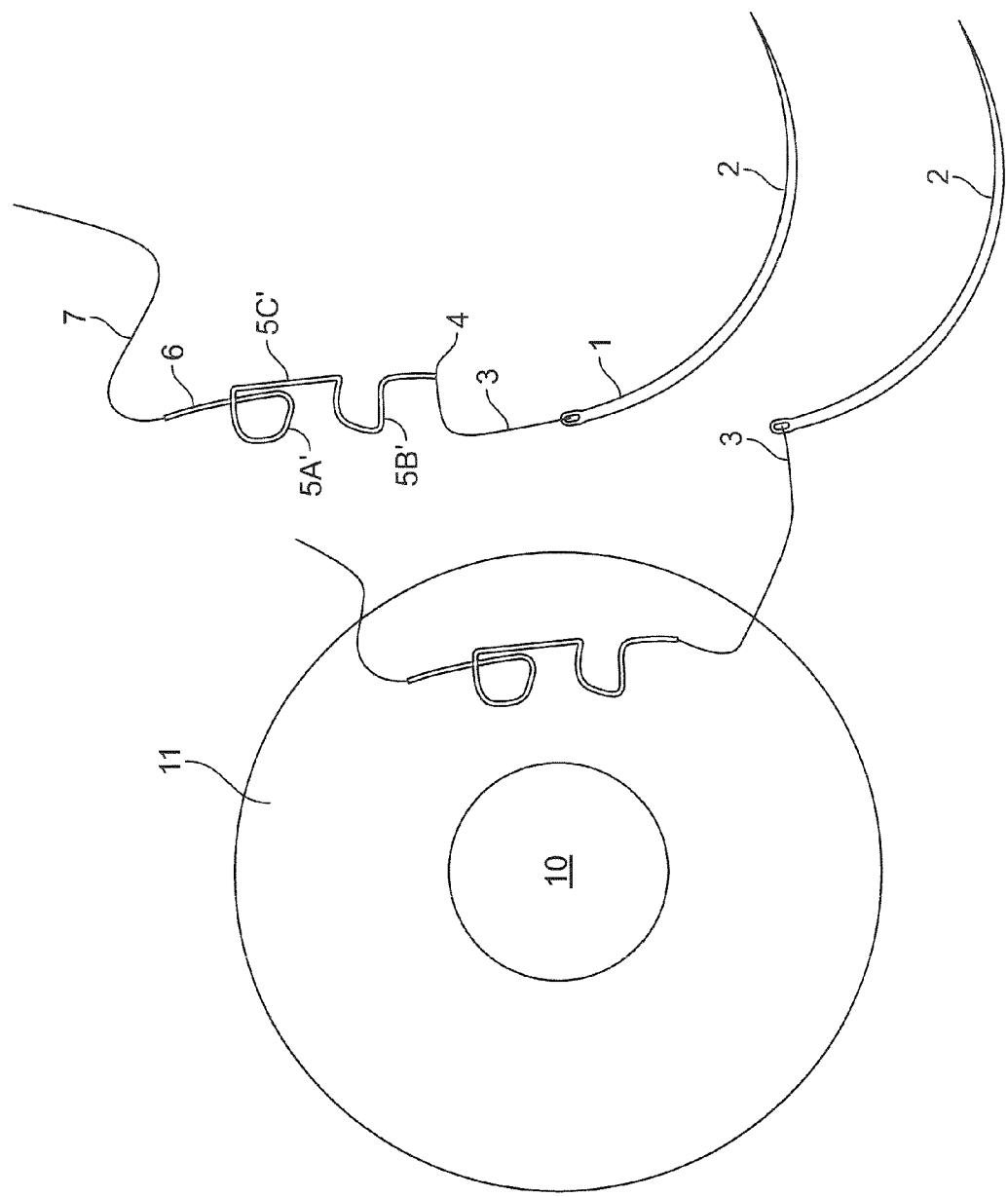
FIG. 4 is a front elevation view which schematically illustrates the placement of the retractor in the anterior chamber of the eye.

FIG. 4 is a front view showing the iris 11, pupil 10 and the retractor 5 installed in the anterior chamber 9. The sutures 3 and 7 extend outside the cornea.

As previously explained, after the needle 1 has entered the anterior chamber, the needle exits from the anterior chamber at an exit site several millimeters from the entry site. Thus the retractor has been introduced into the anterior chamber and the sutures 3 and 7 extend out of the cornea.

FIG. 4 shows a modified embodiment of the retractor 5' on enlarged scale in front of iris 11 with pupil 10. The retractor has been shown with its loops turned 90 degrees for purposes of illustration. The retractor has loops 5A' and 5B' connected by connecting portion 5C'. The retractor can be manipulated to be adjacent to the pupil whereafter the retractor can be displaced into the pupil by means of a hook 13 (FIG. 5B) the hook is inserted into the anterior chamber 9 through a paracentesis (not shown) not requiring a closure stitch. The hook 13 is a conventional means used for various displacement purposes in the eye during surgery.

Figure 5C:
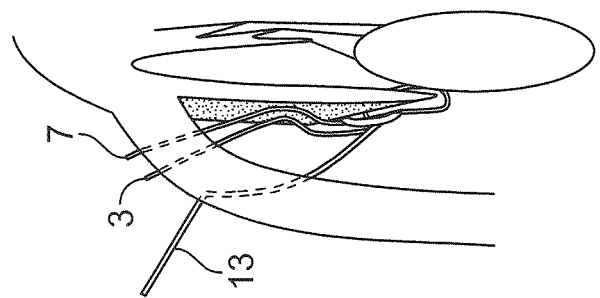
FIG. 5C shows the final position of the speculum.
Figure 5B:
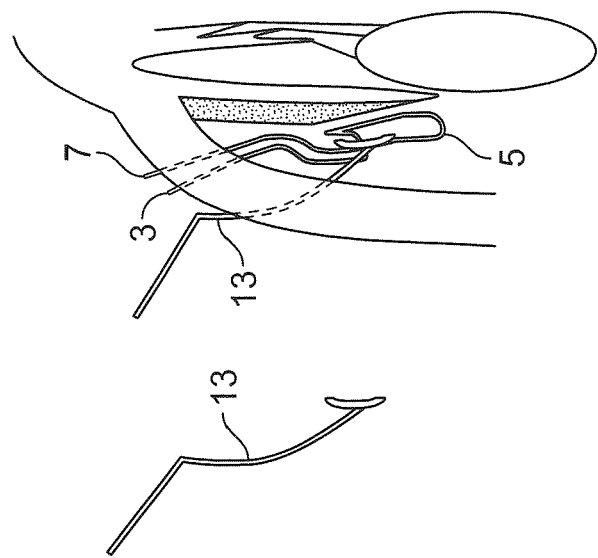
FIG. 5B shows the placement of the speculum into the peri-pupillary space.
Figure 5A:
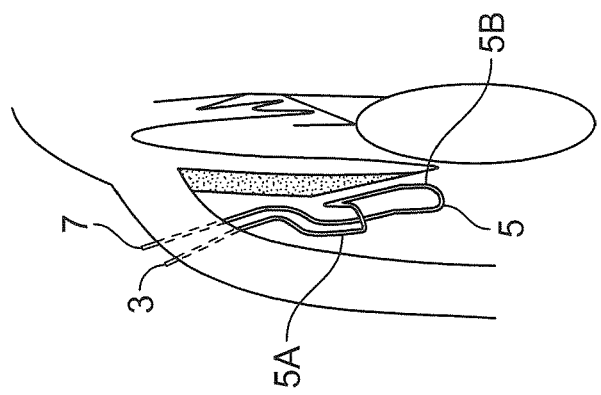
FIG. 5A diagrammatically illustrates the placement of the speculum into the anterior chamber.
Figure 9:
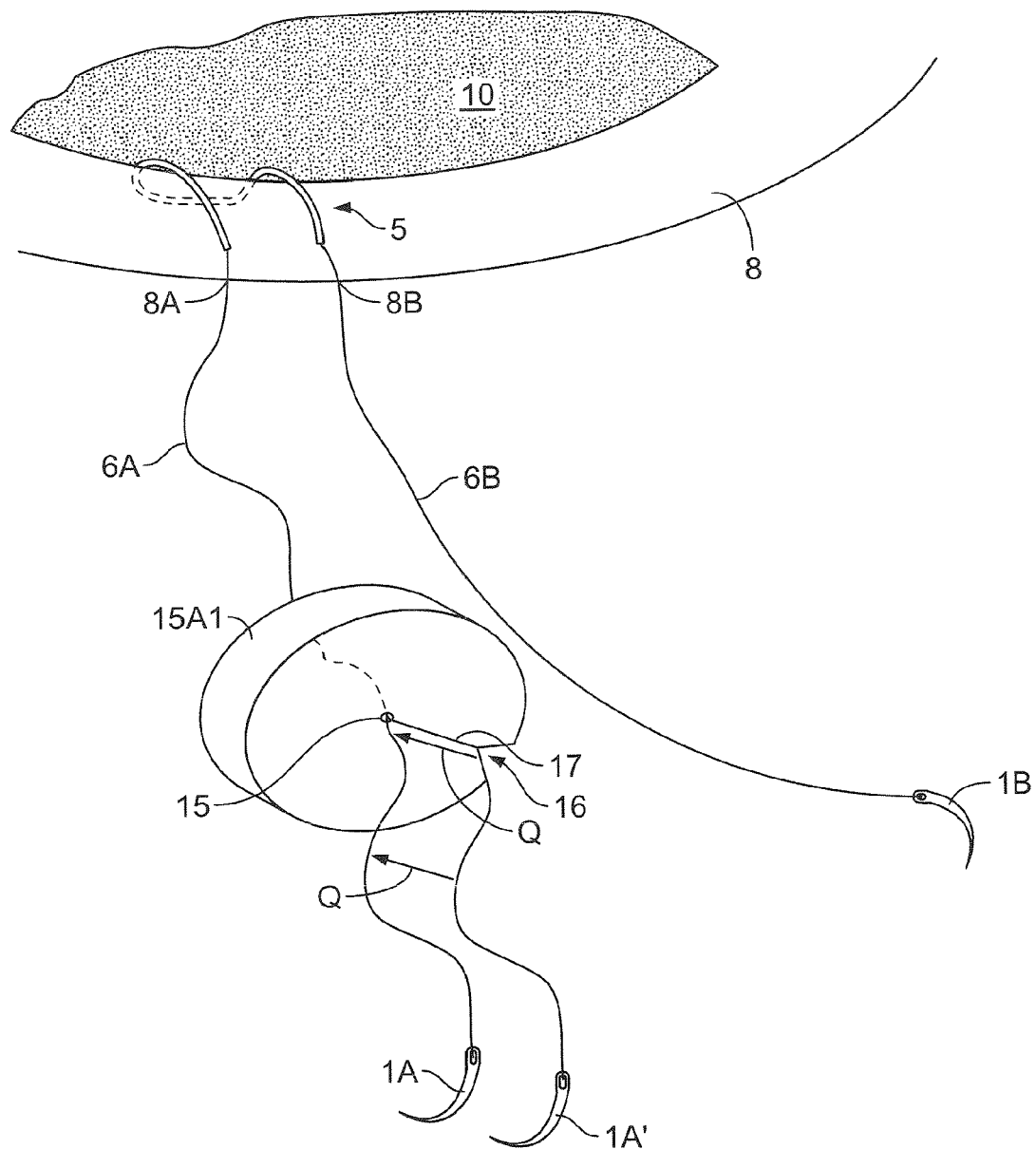
FIG. 9 diagrammatically illustrates a single suture cinch lock for a retractor in operative position dilating an iris.

FIG. 5A shows the retractor in front of and spaced from the pupil and anterior to lens 14, in a position in which the openings in the loops 5A' and 5B' face the edge of the iris with the legs of the loops in a position to straddle the iris so that when the retractor is pulled up, as will be explained later, the loops can engage around the inner peripheral edge of the iris surrounding the pupil. FIG. 9 more clearly shows the engagement of the loops of the retractor with the iris. In order to retract or stretch the iris and expand the pupil, the ends of the sutures are pulled up to apply pressure by the loops 5A' and 5B' against the inner surface of the iris as shown in FIG. 9. FIG. 5B shows a hook 13 engaging the retractor and FIG. 5C shows the hook having pushed the retractor into the pupil.

FIG. 6 diagrammatically shows four substantially equally spaced retractors 5. The retractors 5 are turned 90 degrees for purposes of illustration. The retractors 5 are engaging iris 11 to dilate the pupil when the retractors are in place in the pupil and their sutures are pulled up.

FIG. 7 shows a speculum retractor 20 showing loops 21, the retractor being connected at its ends to sutures 3 and 7.

FIGS. 7A-7D illustrate the use of the retractor for tissue retraction.

In FIG. 7A the needle is shown penetrating and exiting a tissue. The retractor has not yet been used. In FIG. 7B the retractor is shown in position with the sutures in place. In FIG. 7C the retractors were in position prior to retracting the wound on either side of the vertical incision. In FIG. 7D the wound is retracted on either side by the sutures. FIG. 7E shows the retractor in place in cross sectional view.

Figure 8:
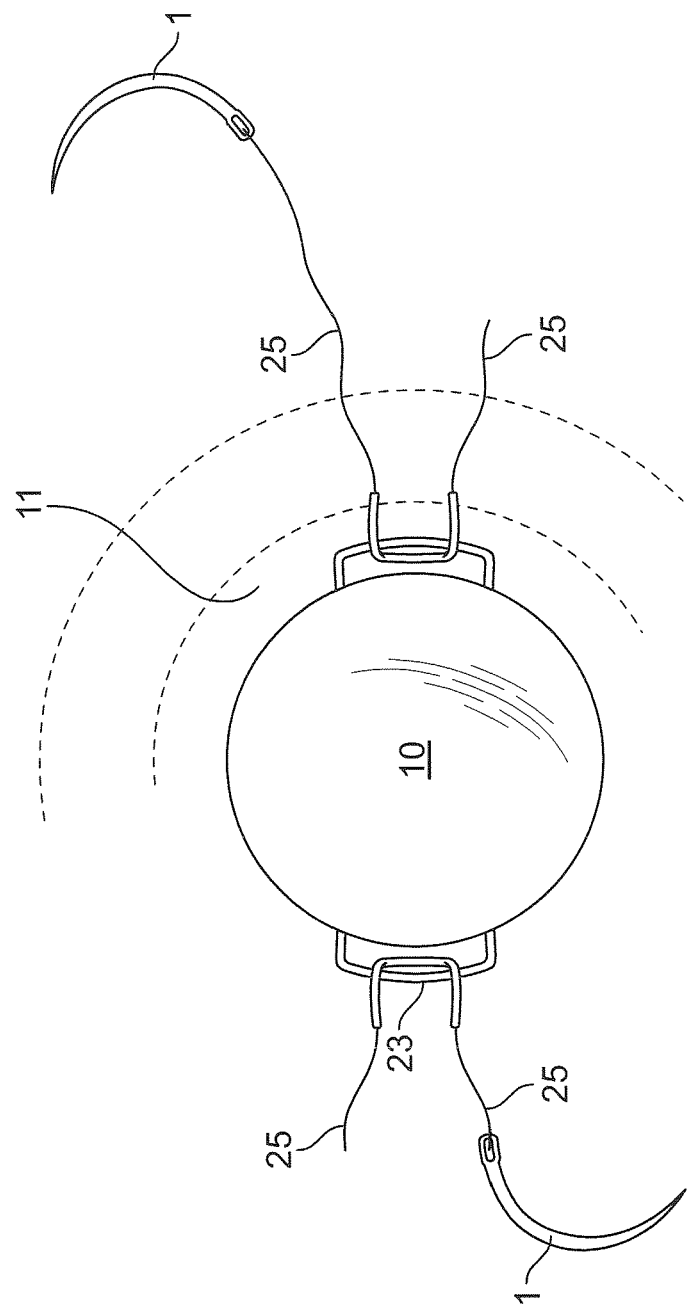
FIG. 8 is a rear elevation view that diagrammatically illustrates the retractor as a docking member for an intraocular lens.

FIG. 8 shows an intraocular lens (IOL) where haptics 23 are extensions that allow docking with modified speculum retractors which are anchored in the cornea or sclera allowing fixation of the implant without suturing the implant directly. The loops of the retractor are shown turned 90 degrees for purposes of illustration, but it is to be understood when installed the legs of the loops will straddle the leg of the haptic.

FIG. 9 shows the iris retractor 5 in place in a dilated pupil 10 engaging the peripheral iris 11. The sutures 6A and 6B pass through the cornea at 8A and 8B respectively. The suture 6A is shown with the needle 1A engaging the indentation of a suture cinch lock disc 15A1 at 16 and passing through a slit 17 that extends from the indentation to a hole 15. The movement of the suture from the indentation 16 to the hole 15 passes across a path Q with the needle moving from 1A' to 1A. The suture 6B and needle 1B have not engaged into the hole 15 in this view.

FIGS. 10A-10G illustrate a single and double lock suture cinch disc 15A1.

Figure 10A:
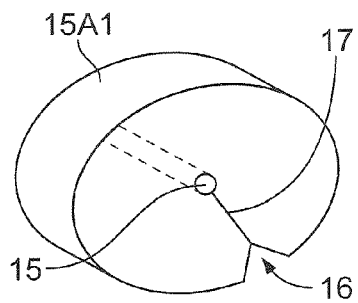
FIG. 10A is a top perspective view of a single cinch lock disc.

FIG. 10A is a top perspective view of a single suture cinch lock disc 15A1 having a single indent 16, a single slit 17 and a single hole 15.

Figure 10B:
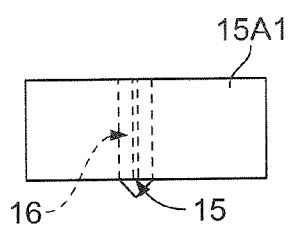
FIG. 10B is a side view of a single cinch lock disc.

FIG. 10B is a side view of a single suture cinch lock disc 15A1 with a single indent 16, single slit 17 and single hole 15.

Figure 10C:
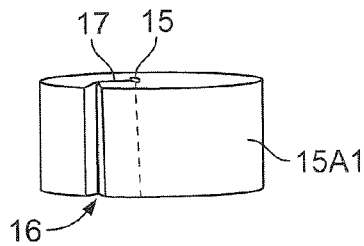
FIG. 10C is a side perspective view of a single suture cinch lock disc.

FIG. 10C is a side perspective view of a single suture cinch lock disc 15A1 with a single indent 16, single slit 17 and single hole 15.

Figure 10D:
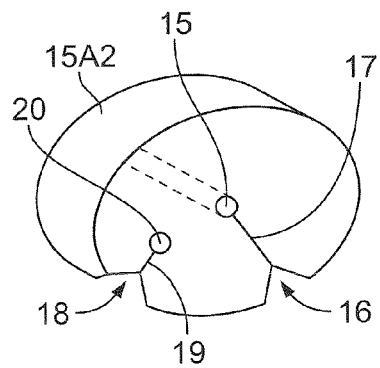
FIG. 10D is a top perspective view of a double suture cinch lock disc.

FIG. 10D is a top perspective view of a double suture cinch lock disc 15A2 with two indents 16, 18, two slits 17, 19 and two holes 15 and 20.

Figure 10E:
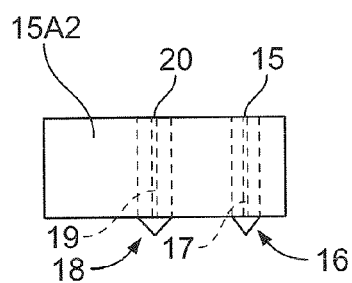
FIG. 10E is a side view of a double suture cinch lock disc.

FIG. 10E is al side view of a double suture cinch lock disc 15A2 with two indents 16, 18, two slits 17, 19 and two holes 15 and 20.

Figure 10F:
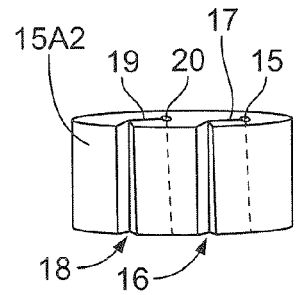
FIG. 10F is a side perspective view of a double suture cinch lock disc.

FIG. 10F is a side perspective view of a double suture cinch lock disc 15A2 with two indents 16, 18, two slits 17, 19 and two holes 15 and 20.

Figure 10G:
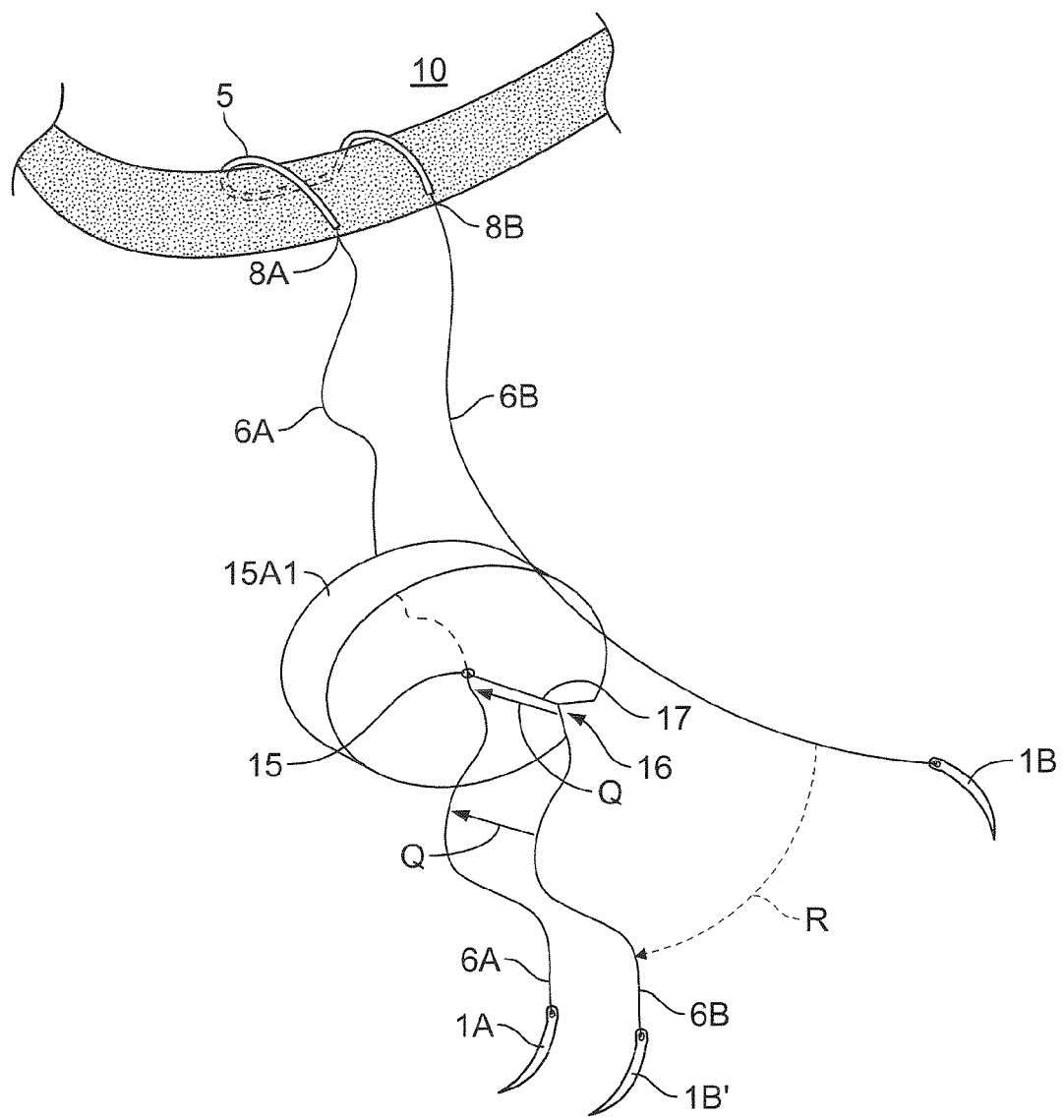
FIG. 10G is a diagrammatic view of the suture retractor in the pupil in place and retracting the iris and secured by the cinch lock disc.

FIG. 10G is a diagrammatic illustration of the suture retractor 5 in the pupil 7 in place and retracting the iris 7A. The sutures 6A and 6B are connected to the retractor and pass through the cornea at 8A and 8B respectively. The needle 1A is shown already having been placed through the hole 15 of suture cinch lock disc 15A2. The suture 6B and needle 1B move into the indent at 16 through arc R into the slit 17 and into the hole 15 across path Q with the suture needle arriving at position 1B'.

Figure 11:
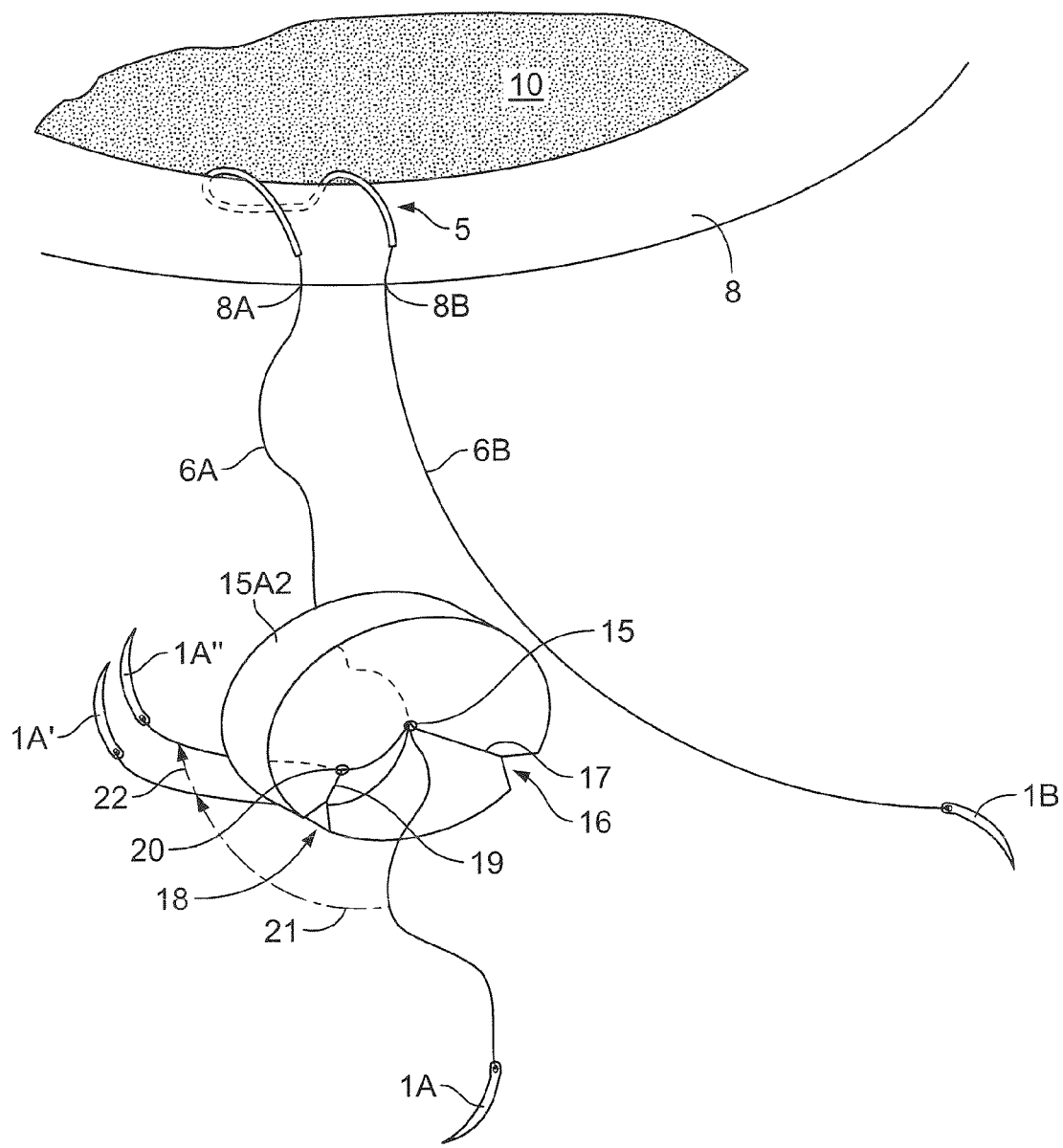
FIG. 11 is similar to FIG. 10G but showing double locking and cinching of the suture.

FIG. 11 is a diagrammatic illustration similar to FIG. 10G showing the suture retractor 5 in the pupil 7 in place and retracting the iris 7A. The sutures 6A and 6B are connected to the retractor and pass through the cornea at 8A and 8B respectively. The needle 1A is shown already having been placed through the hole 15 of suture cinch lock disc 15A2. The suture 6A and needle 1A move into the indent at 18 through arc 21 and needle at 1A', into the slit 19 and into the hole 20 across path 22 with the suture needle arriving at position 1A" with the suture 6A engaged in hole 20 effectively double locking and cinching the suture. The suture 6B has not been engaged in 15A in FIG. 11.

Figure 12:
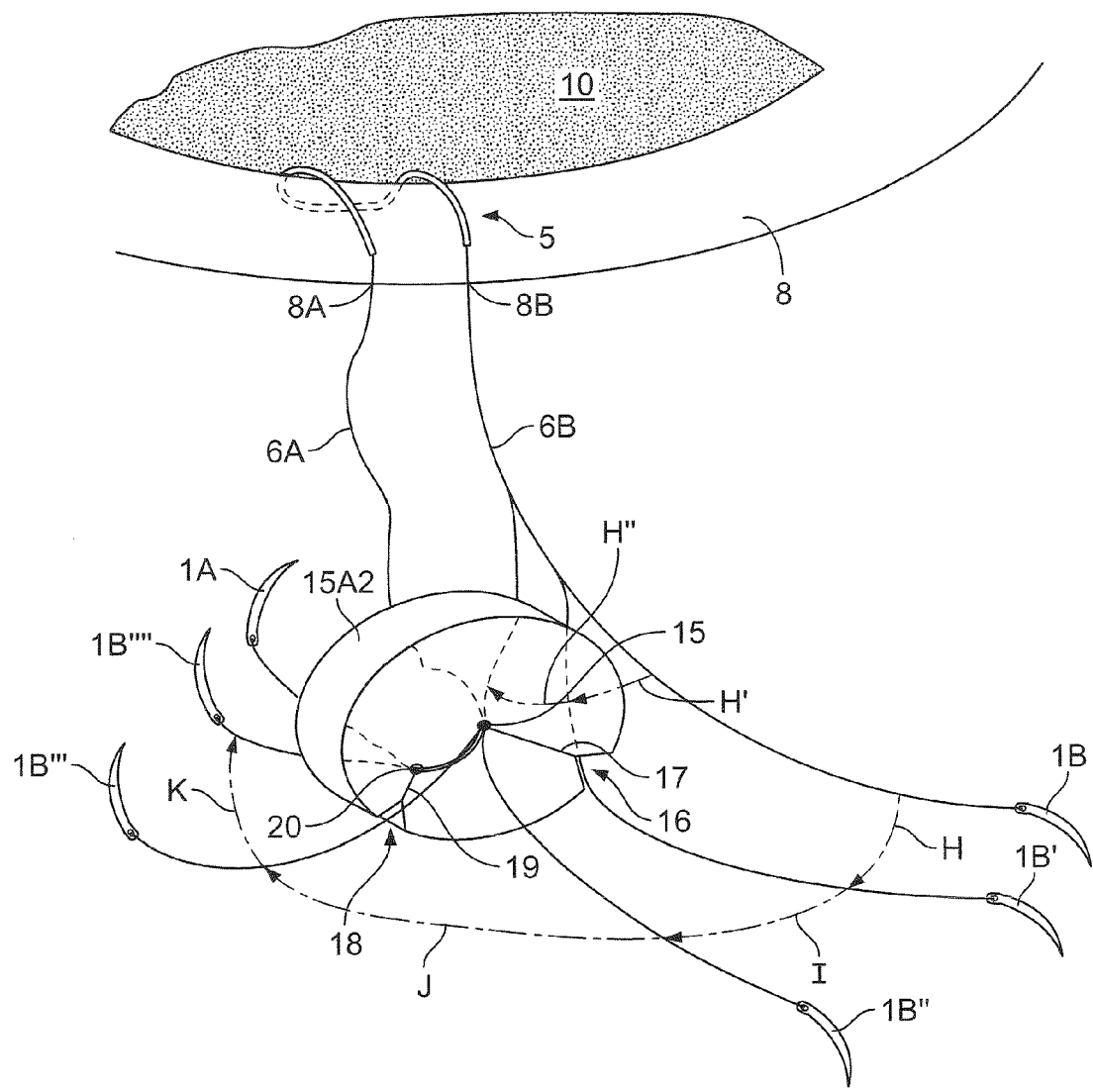
FIG. 12 is similar to FIG. 11 and shows a modification in the double locking and cinching of the suture.

FIG. 12 is a diagrammatic view similar to FIG. 11 with the suture retractor 5 in the pupil 7 in place and retracting the iris 7A. The sutures 6A and 6B are connected to the retractor and pass through the cornea at 8A and 8B respectively. The needle 1A is shown already having been placed through the hole 15 of suture cinch lock disc 15A2. The suture 6A and needle 1A are shown in the final position of FIG. 11. Suture 6B and needle 1B move into the indent at 16 through arc H and needle at 1B', into the slit 17 and into the hole 15 across path I with the suture needle arriving at position 1B". The suture 6B is then moved across path J to engage the indent at 18, the slit at 19 and hole at 20 with needle and suture path K and needle moving from 1B'" to 1B"" with the suture 6B engaged in hole 20 effectively double locking and cinching the suture. The sutures 6A and 6B are both now double locked.

Figure 13A:
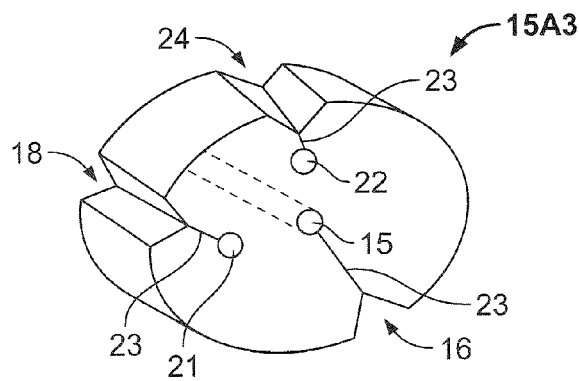
FIGS. 13A-13L diagrammatically illustrate variations of the suture cinch lock disc.

FIG. 13A is a top perspective view of a triple suture cinch lock disc 15A3 with three indents 16, 18, 24, three slits 23 and three holes 15, 21 and 22.

Figure 13B:
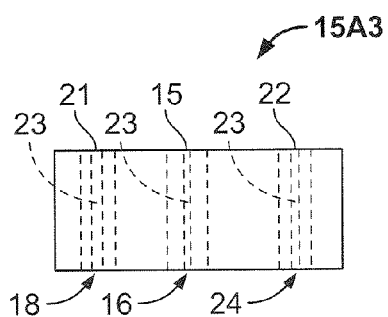

FIG. 13B is a side view of the triple suture cinch lock disc 15A3 with three indents 16, 18, 24, three slits 23 and three holes 15, 21 and 22.

Figure 13C:
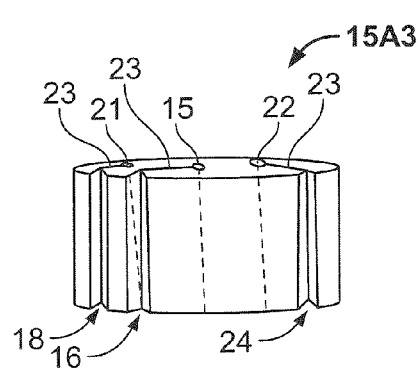

FIG. 13C is a side perspective view of the triple suture cinch lock disc 15A3 with three indents 16, 18, 24, three slits 23, and three holes 15, 21 and 22.

Figure 13D:
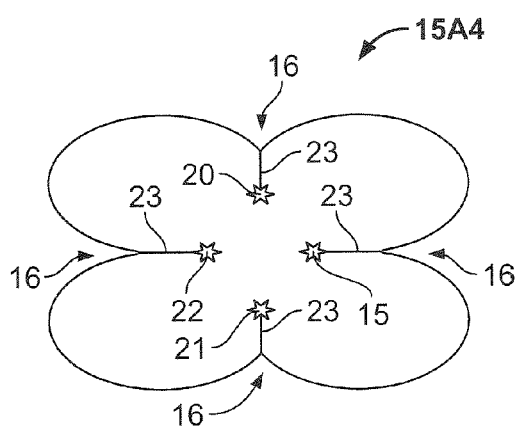

FIG. 13D is a top view of a quadruple clover leaf shaped suture cinch lock disc 15A4 with four indents 16, four slits 23, and four holes 15, 20, 21 and 22.

Figure 13E:
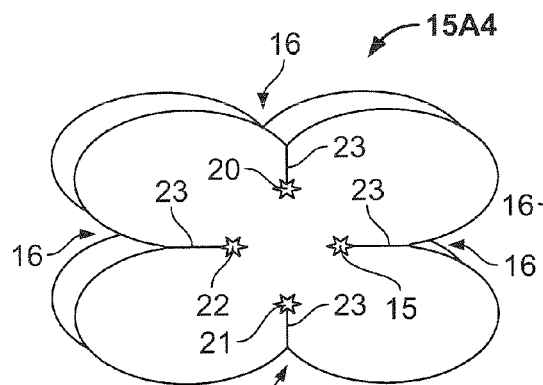

FIG. 13E is a top perspective view of the quadruple clover leaf shaped suture cinch lock disc 15A4 with four indents 16, four slits 23, and four holes 15, 20, 21 and 22.

Figure 13F:
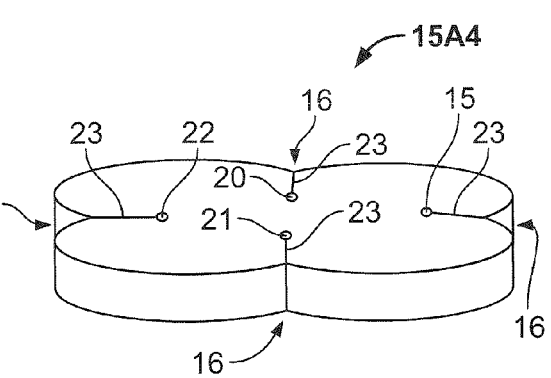

FIG. 13F is a side perspective view of the quadruple clover leaf shaped suture cinch lock disc 15A4 with four indents 16, four slits 23, and four holes 15, 20, 21 and 22.

Figure 13G:
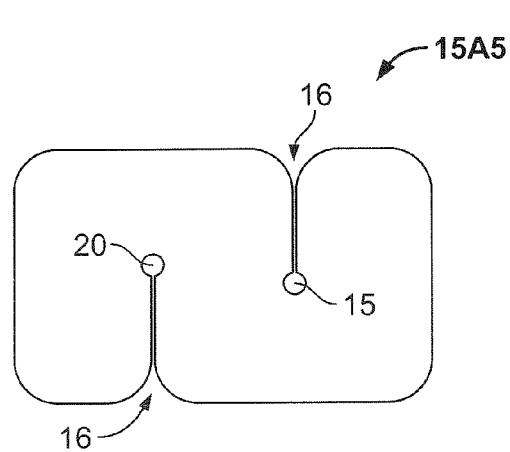

FIG. 13G is a top view of an S shaped double suture cinch lock disc 15A5 with four indents 16, four slits 23, and four holes 15, 20, 21 and 22.

Figure 13H:
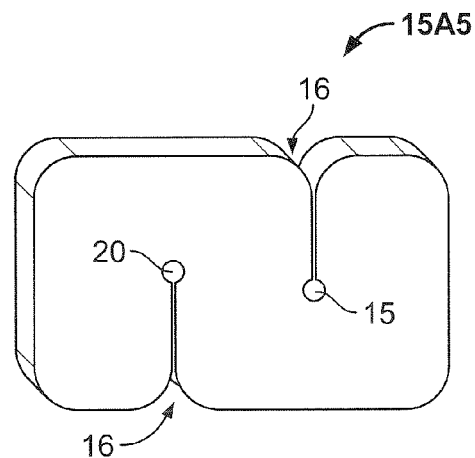

FIG. 13H is a top perspective view of the S shaped double suture cinch lock disc 15A5 with four indents 16, four slits 23, and four holes 15, 20, 21 and 22.

Figure 13I:
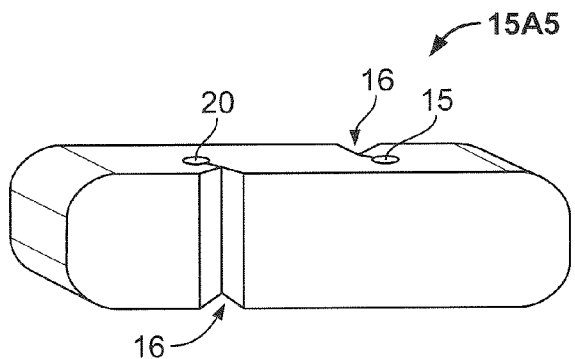

FIG. 13I is a side perspective view of the S shaped double suture cinch lock disc 15A5 with four indents 16, four slits 23, and four holes 15, 20, 21 and 22.

Figure 13J:
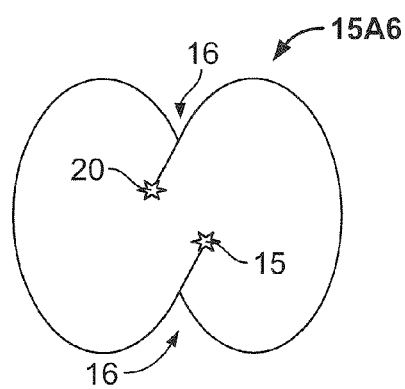

FIG. 13J is a top view of a double oval shaped double suture cinch lock disc 15A6 with four indents 16, four slits 23, and four holes 15, 20, 21 and 22.

Figure 13K:
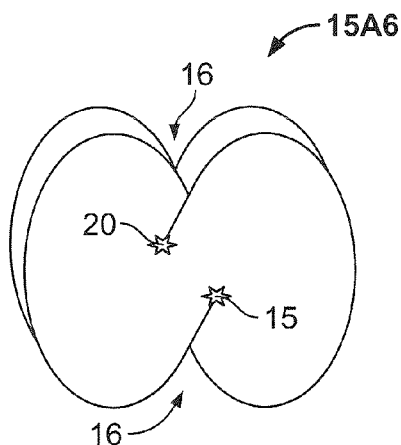

FIG. 13K is a top perspective view of the double oval shaped double suture cinch lock disc 15A6 with four indents 16, four slits 23, and four holes 15, 20, 21 and 22.

Figure 13L:
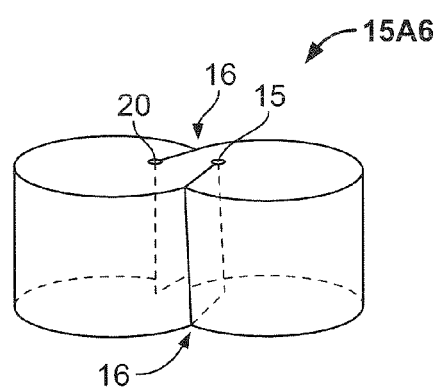

FIG. 13L is a side view of the double oval shaped double suture cinch lock disc 15A6 with four indents 16, four slits 23, and four holes 15, 20, 21 and 22.

Figures 14A, 14B, 14C:
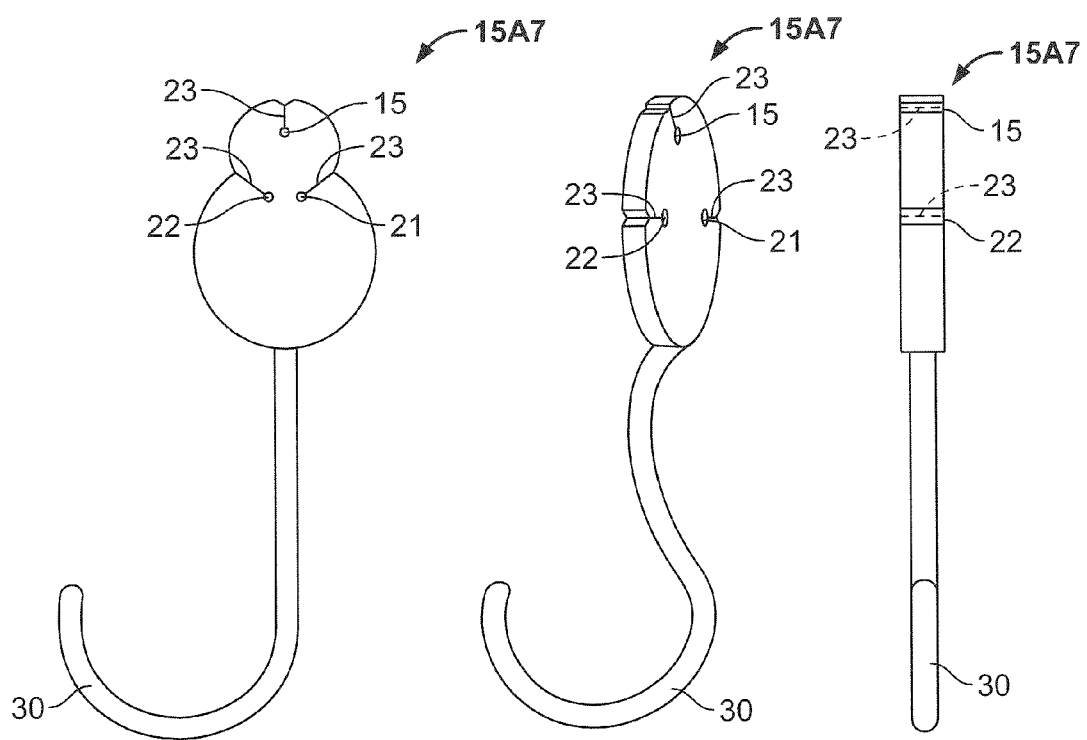
FIGS. 14A-14C diagrammatically illustrate further variations of the suture cinch disc.

FIGS. 14A-14C illustrate a suture cinch lock disc 15A7 with an extension hook like loop 30 which may be attached to a suture loop or clamp to fasten the end distal to the surgical site. The extension may be rigid acting as a hook or flexible allowing the extension to stretch exerting significant traction when fixed under tension.

FIG. 14A is a top view of a disc 15A7 with three slits 23, and three holes at 15, 21 and 22.

FIG. 14B is a side perspective view with three slits 23, and three holes at 15, 21 and 22.

FIG. 14C is a side view with three slits 23, and three holes at 15, 21 and 22.

FIGS. 15A-15C illustrates a suture cinch lock disc 15A8 with an extension hook like loop 31 with a central opening 25 which may be attached to a suture loop, peg or clamp to fasten the end distal to the surgical site. The extension may be rigid acting as a hook or flexible allowing the extension to stretch exerting significant traction when fixed under tension.

FIG. 15A is a two dimensional top view with three slits 23 and three holes at 15, 21 and 22.

FIG. 15B is a side perspective view with three slits 23, and three holes at 15, 21 and 22.

FIG. 15C is a side view with three slits 23, and three holes at 15, 21 and 22.

FIGS. 16A-16C illustrate an adherent means 26 on the back surface of a sure cinch lock disc 15A92. The disc may have a multiplicity of configurations and holes of various sizes to allow for multiple sutures, cords or ropes.

FIG. 16A is a top view showing three slits 23, and three holes at 15, 21 and 22.

FIG. 16B is a side perspective view showing three slits 23, and three holes at 15, 21 and 22.

FIG. 16C is a side view showing three slits 23, and three holes at 15, 21 and 22.

Figure 17A:
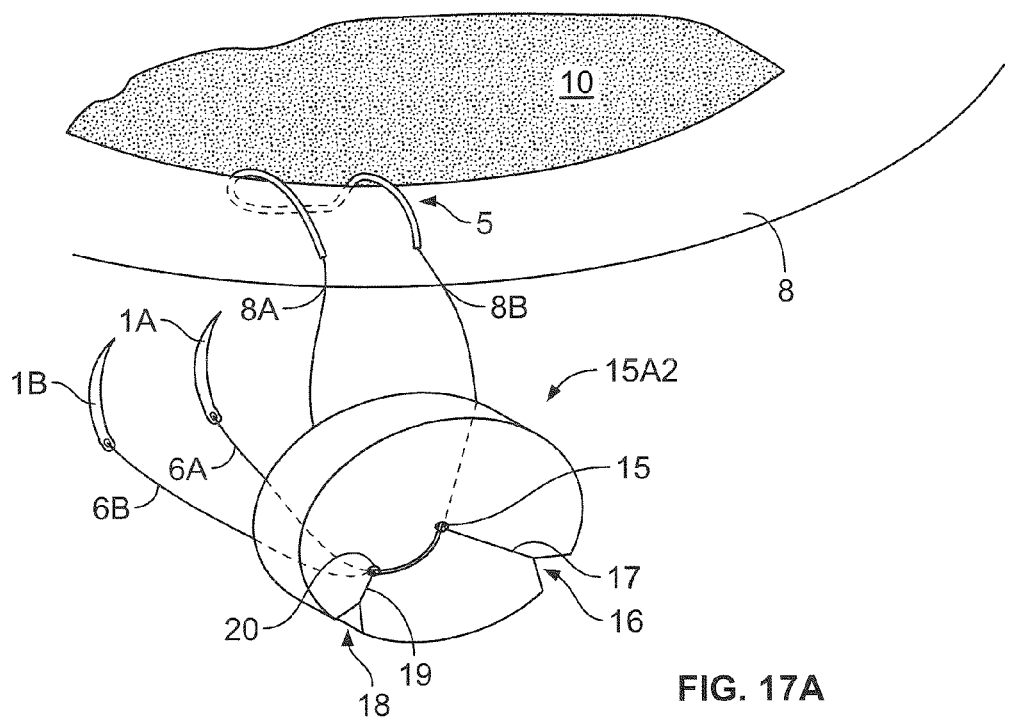
FIGS. 17A and 17B further diagrammatically illustrate the suture cinch lock disc.
Figure 17B:
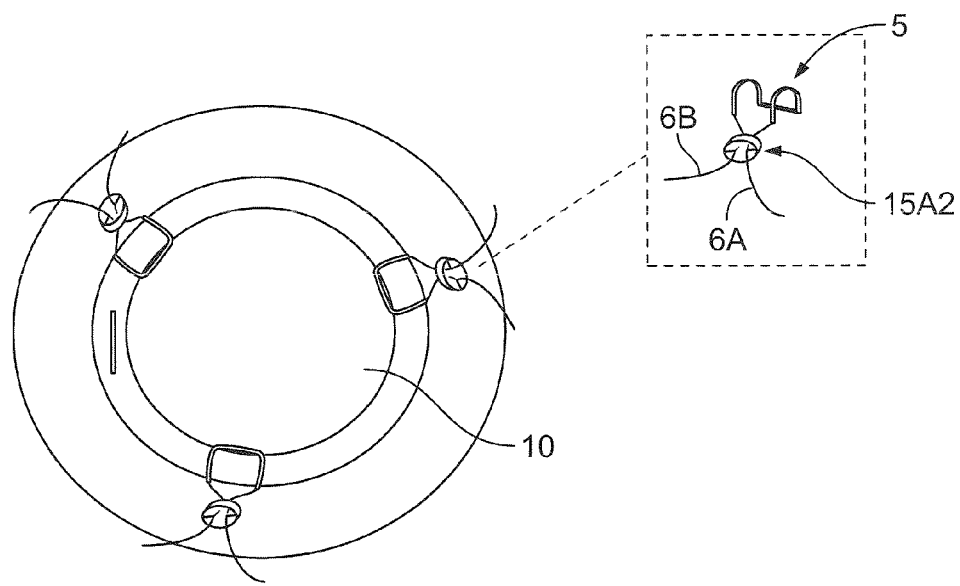

FIGS. 17A and 17B diagrammatically illustrates the suture cinch lock disc in position.

FIG. 17A diagrammatically illustrates, similar to FIG. 11, in which the suture retractor 5 is in the pupil 7 in place and retracting the iris 7A. The sutures 6A and 6B are connected to the retractor and pass through the cornea at 8A and 8B respectively. The needles 1A and 1B are shown already having been placed through the holes 15, 20 of suture cinch lock disc 15A2.

FIG. 17B shows three suture cinch lock discs 15A in position with the retractors 5 retracting the iris 7A and dilating the pupil 7. The inset shows the details of the retractor 5 and the suture cinch lock disc 15A in place.

Figure 18:
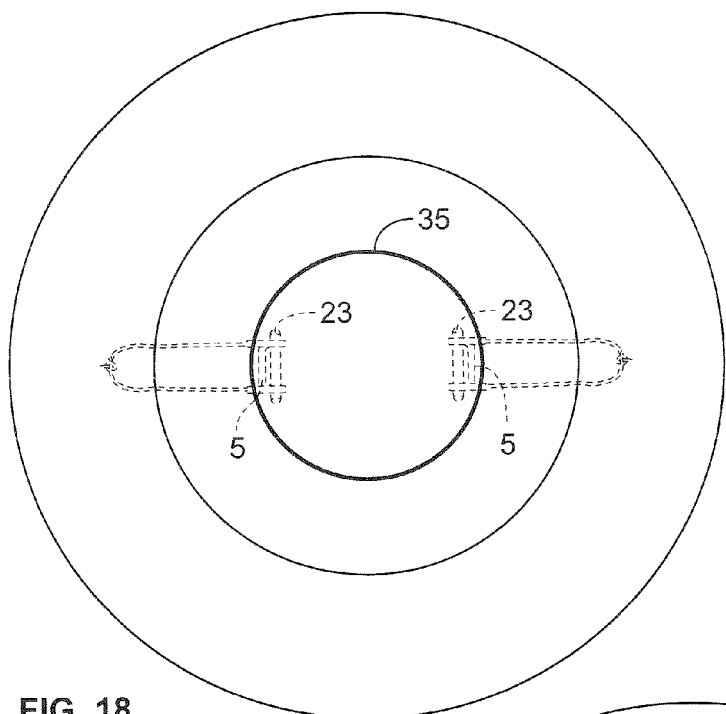
FIGS. 18-20 illustrate an intraocular lens adapted for engagement with the retractor for being secured therewith.

FIG. 18 is a front perspective view of the intraocular lens (IOL) 35 similar to FIG. 8. The haptics 23 are seen on the back surface of the IOL and are engaged by the loops 5A and 5B of the retractors 5. The sutures 3 and 7 are secured to the sclera (not shown) of the eye. The retractors 5 serve as tethers for the IOL.

Figure 19:
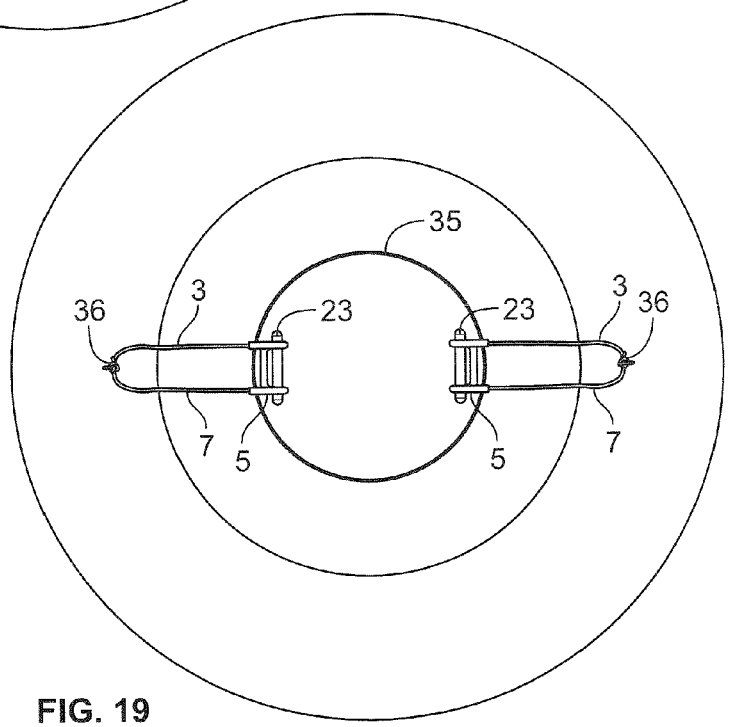

FIG. 19 is a rear view showing the IOL installed in the iris in which the retractors 5, serving as tethers, engage the haptics 23, the ends of sutures 3 and 7 are knotted together at knots 36. The retractors serving as tethers maintain the IOL in place without sulcus or capsule fixation.

Figure 20:
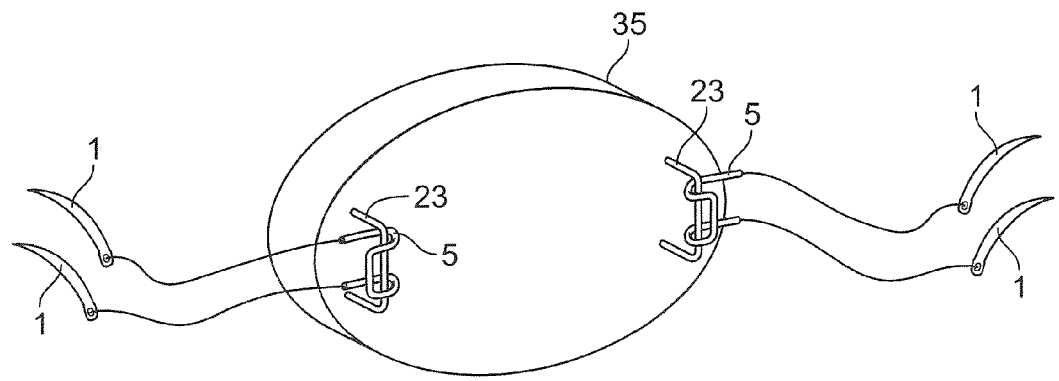

FIG. 20 is a rear perspective view of the IOL showing the engagement of the retractors 8 with the haptics 23. The sutures 3 and 7 are to be secured to the sclera as previously noted.

Figure 21:
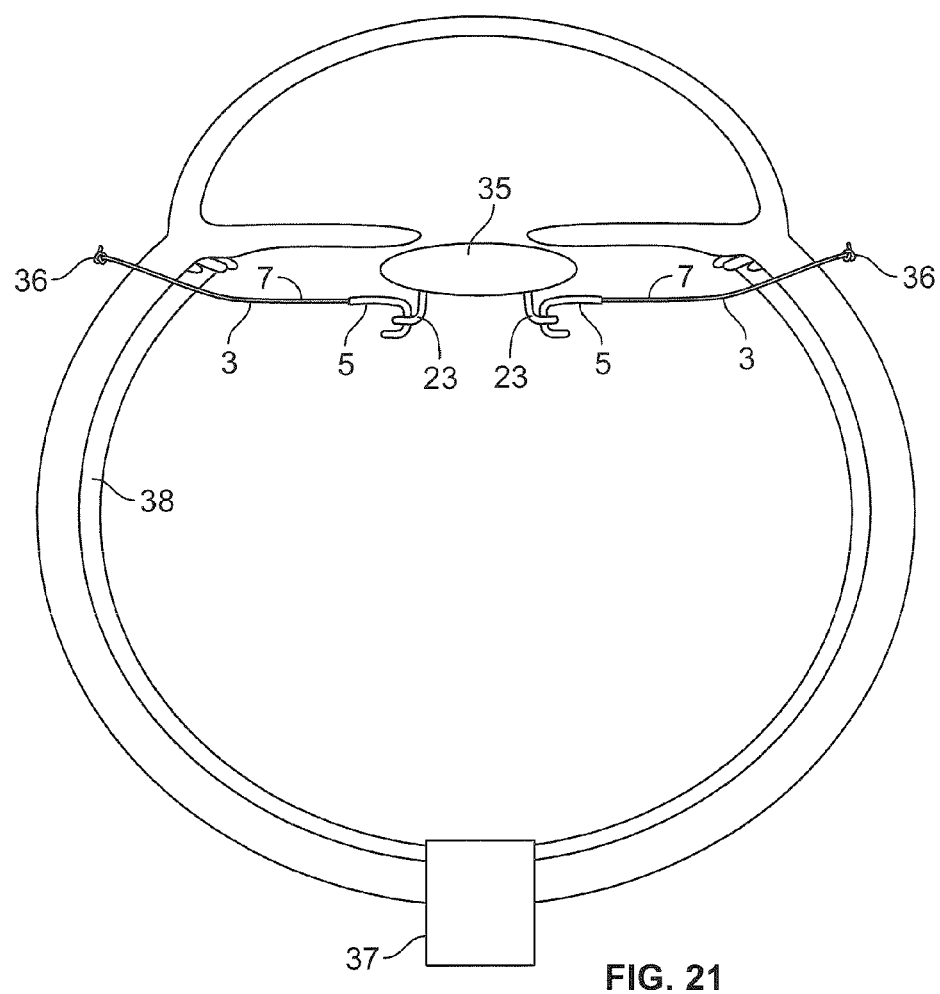
FIG. 21 diagrammatically illustrates a tether secured to a retractor to hold an intraocular lens.

FIG. 21 is an enlarged diagrammatic view of the eye showing the optic nerve 37, the pars plana region of the retina 38 and the IOL installed in the iris. Also visible are the haptics 23 and the retractors 5. The sutures 3 and 7 are knotted at 36.

What is claimed is:

1. Apparatus for insertion into an operative position relative to an aperture within a body of a patient without requiring a closure stitch for entry of the apparatus into the body, said apparatus comprising: a needle for insertion in tissue of the body and forming a needle track in the tissue upon advancement of the needle in the tissue; a treatment device; and means for connecting the treatment device to the needle so that the treatment device can be transported with said needle through said needle track to said operative position, said treatment device comprising a deformable body having shape retentive memory, said deformable body being a wire-form body that forms a plurality of partial loops when in a relaxed state and being deformable to a deformed state wherein the plurality of partial loops of the wire-form body are flattened, said apparatus and needle track being of sufficiently small size so as to permit self-closure of the needle track and not require a closure stitch, wherein said treatment device is adapted for placement in the eye of a patient to dilate a pupil thereof, wherein, in the relaxed state, the wire-form body forms the plurality of partial loops with respective openings of the plurality of partial loops oriented such that each of the respective openings can face an edge of an iris with respective legs of the plurality of loops extending in the same direction for straddling the edge of the iris such that an inner concave surface of the wire-form body can engage the edge of the iris to dilate the pupil of the iris, and wherein, in the relaxed state, said wire-form body forms a straight portion extending uniformly in one direction from a first of the plurality of partial loops to a second of the plurality of partial loops to connect the first and second partial loops.

2. The apparatus as claimed in claim 1, wherein the connecting means comprises a suture connecting said treatment device to said needle to advance the treatment device with the needle.

3. The apparatus as claimed in claim 2, wherein said deformable body of said treatment device has a normal expanded state in said operative position adapted to contact a surface of the aperture in the body to dilate the aperture, said deformable body having a curved surface for contacting the surface of the aperture.

4. The apparatus as claimed in claim 2, wherein the deformable body has first and second ends, the first end being connected to said suture and the second end being connected to another suture.

5. The apparatus as claimed in claim 1, wherein said treatment device is made of a natural biometric material or a synthetic plastic material which is inert to a human body.

6. A method for applying a retraction force to a surface surrounding an opening in the human body comprising the steps of:

(a) providing an apparatus for insertion into an operative position relative to the opening within the body, said apparatus comprising: a needle for insertion in tissue of the body and forming a needle track in the tissue upon advancement of the needle in the tissue; and a treatment device for connecting to said needle for being transported with said needle through said needle track to said operative position, said treatment device comprising a deformable body having shape retentive memory, said treatment device being deformable to a deformed, compacted state when traveling in said needle track and being capable of undergoing shape recovery and expansion when said treatment device reaches said operative position, said needle and its needle track being of small size so as to permit self-closure of the needle track and not require a closure stitch;

(b) advancing the needle through the tissue in the body to an operative position in proximity to the opening, said needle forming the needle track as it advances through the tissue;

(c) connecting a suture to the needle for advancement therewith through the needle track;

(d) securing a speculum in the form of the deformable body having shape retentive memory to the suture for travel therewith through the needle track as the needle advances therein;

(e) deforming said speculum to enable passage thereof through the needle track; said speculum expanding to its original shape to an operative state when the speculum reaches said opening; and (f) engaging said speculum in said operative state with the surface surrounding said opening to apply outward pressure to the surface surrounding the opening, the needle being of sufficiently small size so that the needle track self-closes and does not require a closure stitch.

7. The method as claimed in claim 6, wherein the opening is a pupil in an iris of an eye, the method further comprising dilating the pupil of the iris after the expansion of the speculum to enlarge the pupil.

8. The method as claimed in claim 7, further comprising applying two pressure points by the speculum to the iris to expand the iris.

9. The method as claimed in claim 7, further comprising forming the speculum with a curved surface to contact and expand the iris.

10. The method as claimed in claim 7, further comprising inserting the needle through the cornea of the eye into an anterior chamber of the eye to position the speculum at the pupil and stretching the speculum under tension to its deformed state so that the speculum passes through the needle track.

11. The method as claimed in claim 7, wherein the method is performed while an intraocular lens is supported within a lens capsule of the eye of the human body.

12. The method as claimed in claim 11, further comprising applying the speculum as a tether to stabilize the intraocular lens in its position in the lens capsule.

13. The method as claimed in claim 6, wherein the opening is a pupil in an iris of an eye, said method further comprising connecting a suture to one end of the deformable body to connect the deformable body to the needle, connecting an opposite end of the deformable body to a second suture, the needle entering a cornea, constituting the tissue, at an entry site to enter an anterior chamber of the eye and exiting at an exit site in the cornea, applying the speculum as a tether to an intraocular lens with the sutures exerting traction on the speculum and the pupil by pulling on the sutures distal to the entry and exit sites of the cornea.

14. The method as claimed in claim 6, comprising connecting a suture to one end of the deformable body to connect the deformable body to the needle, connecting an opposite end of the deformable body to a second suture, the needle entering a cornea, constituting the tissue, at an entry site to enter an anterior chamber of the eye and exiting at an exit site, and securing the speculum in the eye as a tether for an intraocular lens while applying tension to the sutures.

15. The method as claimed in claim 13, further comprising anchoring the sutures exerting traction to locking devices which maintain the position of the speculum without being held manually.

16. The method as claimed in claim 11, further comprising docking the speculum with the intraocular lens in a stable state without support by the lens capsule or the iris of the eye.

17. The method as claimed in claim 15, further comprising forming said locking devices as cinch locking discs for securing the sutures under tension.

18. An apparatus for insertion into an operative position relative to an aperture within a body of a patient without requiring a closure stitch for entry of the apparatus into the body, said apparatus comprising: a needle for insertion in tissue of the body and forming a needle track in the tissue upon advancement of the needle in the tissue; a treatment device; and means for connecting the treatment device to the needle so that the treatment device can be transported with said needle through said needle track to said operative position, said treatment device comprising a deformable body having shape retentive memory, said deformable body being a wire-form body that forms a plurality of partial loops when in a relaxed state and being deformable to a deformed state wherein the plurality of partial loops of the wire-form body are flattened, said apparatus and needle track being of sufficiently small size so as to permit self-closure of the needle track and not require a closure stitch, wherein said treatment device is adapted for placement in the eye of a patient to dilate a pupil thereof, wherein, in the relaxed state, the wire-form body forms the plurality of partial loops with respective openings of the plurality of partial loops oriented such that each of the respective openings can face an edge of an iris with respective legs of the plurality of partial loops extending in the same direction for straddling the edge of the iris such that an inner concave surface of the wire-form body can engage the edge of the iris to dilate the pupil of the iris, and wherein, in the relaxed state, each of the plurality of partial loops has an end that is connected to a respective suture, the respective ends of the plurality of partial loops being at opposite ends of the wire-form body.

19. The apparatus as claimed in claim 18, wherein, in the relaxed state, said wire-form body forms a straight portion extending uniformly in one direction from a first of the plurality of partial loops to a second of the plurality of partial loops to connect the first and second partial loops.

20. The apparatus as claimed in claim 1, wherein the wire-form body has a diameter that does not exceed 0.2 mm.

21. The apparatus as claimed in claim 18, wherein each of the first and second partial loops is of predominantly open semi-circular shape.

* * * * *